United States Patent [19]

Peterson

[11] Patent Number: 5,759,486
[45] Date of Patent: Jun. 2, 1998

[54] APPARATUS AND METHOD FOR STERILIZATION OF INSTRUMENTS

[75] Inventor: Edward R. Peterson, Lake Jackson, Tex.

[73] Assignee: Bill F. McGraw, Trustee, Jasper, Tex.

[21] Appl. No.: 622,163

[22] Filed: Mar. 27, 1996

[51] Int. Cl.$^6$ .................................................. A61L 2/00
[52] U.S. Cl. .................... 422/21; 219/687; 219/702; 422/28; 422/38; 422/292; 422/300; 422/307; 422/308
[58] Field of Search ........................ 422/21, 28, 38, 422/292, 300, 301, 307, 308; 219/678, 679, 687, 702, 762, 763

[56] References Cited

U.S. PATENT DOCUMENTS

| | | |
|---|---|---|
| 3,725,003 | 4/1973 | Moore et al. |
| 3,753,651 | 8/1973 | Boucher ........................ 99/217 |
| 3,809,845 | 5/1974 | Stenstrom .................. 219/10.55 |
| 4,393,088 | 7/1983 | Matsusaka .................... 426/234 |
| 4,892,706 | 1/1990 | Kralovic et al. ............. 422/292 X |
| 4,994,237 | 2/1991 | Login et al. |
| 5,019,344 | 5/1991 | Kutner |
| 5,164,166 | 11/1992 | Stepanski et al. |
| 5,215,715 | 6/1993 | Haswell et al. |
| 5,246,674 | 9/1993 | Katschnig et al. |
| 5,248,478 | 9/1993 | Kutner et al. |
| 5,344,493 | 9/1994 | Jackson |
| 5,407,641 | 4/1995 | Katschnig et al. |
| 5,413,757 | 5/1995 | Kutner et al. |
| 5,425,815 | 6/1995 | Parker et al. ............... 422/28 X |
| 5,453,245 | 9/1995 | Kirschner et al. ............. 422/28 |

*Primary Examiner*—Krisanne Thornton
*Attorney, Agent, or Firm*—Bell, Boyd & Lloyd

[57] ABSTRACT

The present invention reveals an apparatus and method for sterilizing instruments at atmospheric pressure in a microwave oven. The apparatus is made of a tray for holding medical, surgical, dental, veterinary, or other instruments, a receiver for holding the tray, three containers, where one container holds a sterilization chemical and a second container holds sterile water, a cover for placement over the tray, and two pumps for transferring the liquids. The method requires a sterilization chemical that has a boiling point of greater than 100° C. and that is at least slightly soluble or is rinsable in water. In addition, the entire microwave sterilization process is completed in less than six minutes.

22 Claims, 3 Drawing Sheets

APPARATUS AND METHOD FOR STERILIZATION OF INSTRUMENTS

BACKGROUND OF THE INVENTION

1. Field of the Invention

The present invention reveals an apparatus and method for sterilizing instruments at atmospheric pressure in a microwave oven.

The apparatus is comprised of a tray for holding medical, surgical, dental, veterinary, or other instruments, a receiver for holding the tray, three containers, where one container holds a sterilization chemical and a second container holds sterile water, a cover for placement over the tray, and two pumps for transferring the liquids.

The method requires a sterilization chemical that has a boiling point greater than 100° C. and that is at least slightly soluble or is rinsable in water. The chemical used may contain water due to addition, contamination, or absorption from air, but will be less than 50% water. Attributes of the chemical used include higher electrical resistance, higher thermal resistance, and lower volatility when compared to water or weak solutions comprised mostly of water. In addition, desirable properties of the sterilization chemical include higher viscosity and lower heat capacity than water. The entire microwave sterilization process is preferably completed in less than ten minutes.

2. Description of the Related Art

Sterilization is defined as the complete destruction of microorganisms by heat (wet steam under pressure at 120° C. for 15 minutes, or dry heat at 360°–380° C. for three hours) or by bactericidal chemical compounds (cold immersion methods). Heat sterilization methods, such as steam heat (autoclave), dry heat, and chemical vapor are generally preferred over the cold immersion methods which are usually not effective unless glutaraldehyde is used and the instrument is immersed for 7–10 hours.

It has been thought that sterilization of viruses could be accomplished by conventional sterilization techniques such as boiling tools or instruments in water. However, studies have shown that many viruses are more heat resistant than bacteria and that as much as 80% of the equipment used for sterilization of medical equipment and tools are not run at a sufficiently high temperature to inactivate and/or kill these viruses.

Present sterilization techniques for medical tools employ steam under pressure. The steam is applied at pressure by using an autoclave. Autoclaves are, in essence, pressure cookers that allow water to be heated to higher temperatures. An autoclave consists of an empty chamber, generally made from stainless steel, with a method for adding water under pressure to the chamber, heating coils, and a pressure relief valve so that a given pressure may be maintained.

The operational temperature of an autoclave is generally a compromise. The higher the pressure, the sturdier the chamber must be made, which raises the cost and the mass of the system. Since higher pressures allow higher operational temperatures, the sterilization time required at high temperatures is reduced, so the medical equipment can be returned to service faster, which is highly desirable. However, the more massive the system is, the longer the time is required for the system to heat and cool. In some of the faster equipment, the time between putting a tool into an autoclave and being able to return it to service is 45 minutes even though the actual sterilization time may be as little as 15 minutes.

Higher temperatures ensure the efficiency of the sterilization process. However, the most common method for attaining higher sterilization temperatures is to heat water under increased pressures. However, high temperature water under pressure can be dangerous. Table I lists the boiling temperature in both degrees Fahrenheit (°F.) and Centigrade (°C.) of water at different pressures shown in pounds per square inch (PSIA) and atmospheres (ATM).

TABLE I

| WATER PRESSURE | | | |
|---|---|---|---|
| Pressure | | Temperature | Temperature |
| (PSIA) | [ATM] | (°F.) | (°C.) |
| 14.7 | [1.0] | 212 | 100 |
| 29.8 | [2.0] | 250 | 121 |
| 45.5 | [3.1] | 275 | 135 |
| 60 | [4.1] | 293 | 145 |
| 169 | [11.5] | 367 | 187 |

This table shows that to reach a temperature of 145° C. in an autoclave using water to form steam, the pressure produced by the steam will be approximately 60 pounds per square inch or 4.1 times normal atmospheric pressure at sea level.

In order to overcome some of the limitations imposed on the sterilization process by the use of high temperature water under pressure, some inventors have explored the use of microwaves. Several methods and apparatuses for sterilization with microwaves have been reported. For example, in Kutner et al. (U.S. Pat. No. 5,413,757) and Kutner et al. (U.S. Pat. No. 5,019,344), each patent discloses a method for sterilizing articles such as dental and medical instruments in a pouch using microwave energy. In these methods, a liquid sterilant is vaporized to produce an atmosphere of hot sterilant vapor. An expandable pouch that is gas tight and transparent to microwave energy is used. The pouch must be able to expand to a visually distended condition. Thus, these patents disclose methods for vapor sterilization under pressure.

Katschnig et al. (U.S. Pat. No. 5,407,641) and Katschnig et al. (U.S. Pat. No. 5,246,674) each disclose a microwave apparatus for disinfecting or sterilizing. The apparatus may include an injector for the addition of water or another liquid. However, U.S. Pat. No. 5,407,641 only teaches adding a disinfectant such as citric acid or lemon oil. The purpose of adding water or liquid is for preventing the treated material from burning and the purpose for adding lemon oil and citric acid is that they may act as odorants and disinfectants.

The injector in U.S. Pat. No. 5,407,641 is referred to as "the water injector" and the purpose of the injector is to put water into the container and not another liquid, other than as an additive. The addition of disinfectant and/or odorants may be carried out in dependence on the amount of injected water as controlled by the microprocessor so as to ensure that the material to be treated includes a sufficient concentration of disinfectant and/or odorant. Although an additive is mentioned, the added liquid is always principally water.

U.S. Pat. No. 5,246,674 discloses a device for use in a microwave apparatus that has an injector for inserting water or other liquid into the material to be treated. In principle, this patent covers a water addition system to impede burning of the contained material, calculating the amount of water to be added by the mass of material to be treated, a weighing apparatus, a nozzle that does not absorb microwave radiation which can monitor pressure, temperature, and other (non-specified) chemical and physical parameters. In practice, the material to be treated is added to the top chamber, the material is exposed to microwave radiation, the weight of the material is measured, and then the liquid is added to effect disinfection or sterilization. Again, the liquid injector supplies water with additives such as odorants or disinfectants to improve sterilization and to prevent burning of the wastes. The additives mentioned again are lemon oil and citric acid.

Jackson (U.S. Pat. No. 5,344,493) discloses a cleaning process using microwaves. More specifically, one or more dense fluids are mixed with one or more chemical agents and are simultaneously subjected to microwave radiation and centrifugal force to remove deeply recessed contaminants from internal and external surfaces of intricately arranged or formulated substrates such as biomaterials, spent activated carbon, elastomerics, surgical aids, or dental implements.

The purpose for introducing a physical or chemical agent into the dense fluid is to cause the precipitation, dissociation, dissolution, or activation of the physical or chemical contaminant in the substrate interstices. The invention uses liquefied and supercritical gases as the dense fluids for cleaning substrates. Dense fluid candidates include carbon dioxide, nitrous oxide, krypton, xenon, argon, oxygen, helium, and nitrogen. The chemical agents added to the dense fluids include organo-metallics, biocides, surfactants, alcohols, dyes, reductants, oxidizers, and odorants.

Kutner et al. (U.S. Pat. No. 5,248,478) discloses a process for disinfecting soft contact lenses using microwaves. However, the process requires that the soft contact lenses be shielded from the microwave electromagnetic radiation. Furthermore, the only disinfecting solutions disclosed are saline, a 3% solution of hydrogen peroxide and an isotonic solution containing boric acid.

Stepanski et al. (U.S. Pat. No. 5,164,166) disclose an apparatus for disinfecting contact lenses by use of microwave energy. The apparatus requires a compartment that shields the contact lenses from the microwave energy. Furthermore, this patent teaches that the disinfecting fluid is typically an aqueous solution containing substantially no or few active ingredients.

Login et al. (U.S. Pat. No. 4,994,237) disclose a method to preserve and sterilize biological tissues by exposing the tissue to microwave irradiation. The biological material is immersed in an osmotically balanced solution and heated to between 35° C. and 50° C. for a given period of time. A number of additives for achieving or maintaining osmotic balance are listed and all are held at less than 1% of the solution concentration.

However, none of the reported patents provide for a high temperature, non-conductive fluid, super heating fluid microwave sterilizer or an atmospheric pressure, high temperature microwave sterilization process.

SUMMARY OF THE INVENTION

The present invention is for an apparatus and method for sterilizing instruments at atmospheric pressure in a microwave oven. The apparatus is comprised of:

a) a tray for holding medical, surgical, dental, veterinary, or other instruments, b) a receiver for holding the tray, the receiver being connected to a first container, a second container and a third container, where the first container holds a sterilization chemical for transfer to the receiver, the second container holds water for transfer to the receiver, and the third container holds sterilization chemical and water for transfer from the receiver, c) a cover for placement over the tray, d) a first pump to transfer sterilization chemical to the receiver, and e) a second pump to transfer water to the receiver.

In one embodiment of the apparatus, a first valve is used to control the transfer of sterilization chemical to the receiver, a second valve is used to control the transfer of water to the receiver, and a third valve is used to control the transfer of sterilization chemical and water from the receiver.

In another embodiment of the apparatus, the receiver or the cover is made from a microwave transparent material and the transparent material is glass, plastic, or ceramic. In another embodiment of the apparatus, the tray, the receiver or the cover is made from a metal.

In a preferred embodiment, the tray and the receiver are made from stainless steel, the cover is made from borosilicate glass, and a metal strip is connected to the stainless steel tray and to the instruments.

The method for sterilizing instruments at atmospheric pressure in a microwave oven is comprised of the following steps:

a) the instruments to be sterilized are placed in a microwave oven;

b) the instruments are immersed in a sterilization chemical, where the sterilization chemical has a boiling point greater than 100° C.;

c) the instruments in the sterilization chemical are subjected to microwave heating;

d) the microwave heating is terminated;

e) the sterilization chemical is drained from the instruments;

f) the instruments are rinsed with sterilized water;

g) the sterilized water is drained from the instruments; and h) sterilized instruments are recovered from the microwave oven.

The sterilization chemical has a boiling point greater than 100° C., preferably at least 121° C., and more preferably at least 140° C. Furthermore, the sterilization chemical is at least slightly soluble in water or is rinsable in water.

In another embodiment of the present method, the sterilization chemical contains an additive to facilitate rinsing away the chemical from the instruments. The additive can be, for example, ethanol or diethylether.

In a preferred embodiment of the present method, the entire microwave sterilization process is completed in less than six minutes.

DETAILED DESCRIPTION OF THE INVENTION

The high temperature, non-conductive fluid, super heating fluid microwave sterilizer and the atmospheric pressure, high temperature microwave sterilization process of the present invention overcome the problems associated with conventional autoclave and microwave sterilization apparatuses and procedures. The fluids used in the present invention do not boil at the temperatures used and there is no need to contain pressure in the sterilization process. The microwave oven does not get hot and is not itself dangerous. Only the fluid and the fluid container with the tools and/or instruments inside get hot. This smaller heated mass means a shorter warm-up time and a shorter cool-down time.

The cool-down time is further reduced by rinsing the tools and/or instruments with sterilized water produced and optionally reproduced within the microwave sterilization system. The water is sterilized by distillation of the chemical/rinse water mixture, which boils at a much higher temperature than ordinary water.

Figure 1:
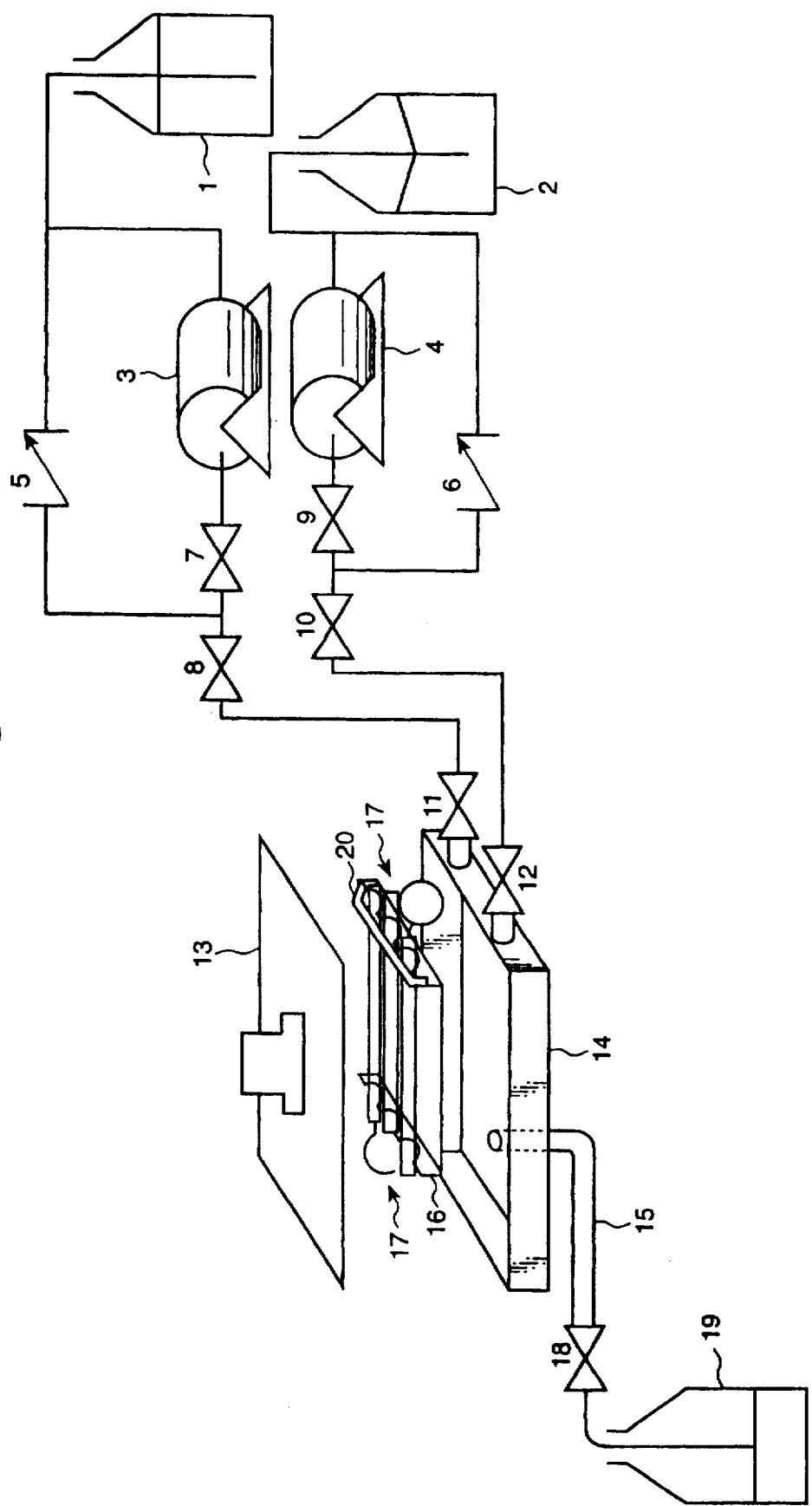
FIG. 1 is a schematic representation of the high temperature, non-conductive fluid, super heating fluid microwave sterilizer of the present invention.

The present invention is shown schematically in FIG. 1. More specifically, a container 1 is filled with a sterilization chemical, i.e., a specific type of chemical for use in the sterilization process. The sterilization chemical in container 1 may be chosen from the list of chemicals in Table II or mixtures of these chemicals or similar chemicals or chemical mixtures that have a boiling point greater than 100° C., preferably 121° C. or greater, more preferably 140° C. or greater, and are at least slightly soluble in or rinsable with water. Thus, the term sterilization chemical, as used in this application, includes mixtures of chemicals having the required properties for functioning in the sterilization process.

Valves 7, 8 and 11 are opened and a pump 3 is activated in order to transfer the sterilization chemical into the receiver 14. A fluid flow check valve 5 is used to control the flow of sterilization chemical from container 1. When a specific volume of sterilization chemical has been transferred into the receiver 14, pump 3 is deactivated and valves 8 and 11 are closed. Microwave power is activated for a long enough period of time to allow the sterilization chemical to reach and maintain a specific temperature for sterilization. Once the specific temperature has been attained, the temperature is maintained for a specific period of time. The entire process for the heating of the sterilization chemical and maintenance of the temperature is referred to as the sterilization heating process.

At the conclusion of the sterilization heating process, i.e., when the temperature has been maintained for the specific period of time, the microwave power is deactivated. Valve 18 is opened and the sterilization chemical is allowed to drain from the receiver 14 into a third container 19.

Once the sterilization liquid has drained from the receiver 14, valves 9, 10 and 12 are opened and a pump 4 is activated in order to transfer sterilized water from container 2 into the receiver 14. A fluid flow check valve 6 is used to control the flow of sterilized water from container 2. The sterilized water rinses the sterilization chemical from the instruments 17 as well as cools them. The sterilized water drains from the receiver 14 into the third container 19, via a drain tube 15.

After the instruments 17 have been rinsed with and cooled by the sterilized water, the cover 13 is removed from the

TABLE II

Exemplary Sterilization Chemicals

| CHEMICAL | BP (C) | MP (C) | SOLUBLE | TOXICITY |
| --- | --- | --- | --- | --- |
| Polyethylene glycol (Mn = 400) | >200 | 6 | water | nontoxic |
| Propylene glycol | 187 | −60 | water | nontoxic |
| Glycerin | 290 | 18 | water | nontoxic |
| Di(propylene glycol) | 233 |  | water | low |
| 2,2-Dimethyl-1-3,butanediol | 202 | −13 | water | low |
| Triethylene glycol | 287 | −7 | water | low |
| Tetraethylene glycol | 327 | −4 | water | low |
| Dimethyl sulfoxide | 189 | 19 | water | low |
| Triethanolamine | 335 | 21 | water | low |
| Triethylcitrate | 294 | −46 | water | low |
| Tetrahydrofurfuryl acetate | 194 | <25 | water | low |
| Thiodiglycol | 283 | −10 | water | low |
| Propyleneglycol phenyl ether | 237 | <25C | water | low |
| 1-Heptanol | 175 | −35 | slightly soluble in water | low |
| Methane Sulfonic acid | 200 | 17 | water | corrosive acid, high |
| Diethylene triamine | 207 | −39 | water | by ingestion, high |
| N,N-Dimethylformamide | 152 | −61 | water | strong irritant |
| Glutaraldehyde | 188 | −14 | water | toxic and irritant |
| Propiolactone | 155 | −33 | water | strong skin irritant |
| Diiodomethane | 181 | 6 | in alcohol, not water | narcotic in high concentrations |

A second container 2 is filled with sterilized water. All valves 7, 8, 9, 10, 11 12 and 18 are set in a closed position. A tray 16 holding medical, surgical, dental, veterinary or other instruments 17 is placed in a receiver 14. A cover 13 is placed over the receiver 14. Optionally, a gasket (not shown) may be inserted or placed between the cover 13 and the receiver 14 in order to form a better liquid seal.

receiver 14. With the cover 13 removed, the tray 16 holding the instruments 17 is removed from the receiver 14.

The chemical heating time required to obtain sterility with the present apparatus and method is between about 4 to 4½ minutes. Fill time with glycol is between about 15 and 25 seconds and fill time with water takes about 5 seconds. Drain time is about 15 seconds. Therefore, current cycle time is between about 4½ and 5¼ minutes. This sterilization time compares to the 25 to 55 minutes routinely encountered using conventional sterilization (autoclave) equipment.

The exemplary sterilization chemicals listed in Table II serve as examples of the range of liquids and chemicals, with ranging chemical functionalities, that meet the needs of the atmospheric pressure high temperature microwave sterilization process. Food grade (or better) oils, resins, waxes, flavorants, gums, essential oils, or other plant and animal products that have a boiling temperature above 100° C. are meant to be included. In some cases, an additive or intermediate material, for example, ethanol, diethylether, etc., may be required to rinse away a water non-soluble substance (e.g., animal fat, corn oil, tallow) prior to the water rinse. The sterilization chemical should contain less than 10% additive by volume.

In the current embodiment, the contents of container 19, i.e., the sterilization chemical and the sterilized water, are not further treated. Additional embodiments of the present invention allow for the sterilization chemical and the sterilized water to be restored to their essentially pure state through distillation, the power being supplied by the same microwave chamber used to perform the sterilization of the instruments 17.

With the present invention, sterilization and distillation cannot be effectively performed at the same time but can be performed separately by the same microwave device. Repurification of the microwave-treated chemical improves the overall efficiency of the sterilization system by allowing the user to buy and to handle less sterilization chemical.

In the present embodiment, the tray 16 and the receiver 14 are made from stainless steel (a non-microwave absorptive metal) and the cover 13 is made from borosilicate glass (a microwave transparent material). The metal tray 16 and receiver 14 allow for rapid cool-down, reduction or elimination of the potential for arcing, and the use of fluids that reach temperatures from greater than 100° C. to greater than 300° C. before boiling. A metal strip 20 is used that is connected to the metal tray 16 to connect to all the metal tools, thereby maintaining the same potential and removing the possibility for arcing.

The tray 16 and the receiver 14 components can also be made from glass, plastic, ceramic or any other microwave transparent material that allows microwaves to penetrate into and heat the sterilization chemical contained in receiver 14. Example of such materials include polyetherimides, polyimides, Kalrez (™) and similar polymers, polytetrafluoroethylene, quartz, Pyrex glass, dense aluminum oxide, etc.

If the receiver 14 is made from glass, plastic, ceramic or any other microwave transparent material, the cover 13 can be made from any non-microwave absorptive metal or microwave transparent material. In no case can the entire container consisting of the receiver 14 and the cover 13 be made from metal that does not absorb microwave energy without a means for introducing microwave energy into the container. The receiver in the present embodiment is not built to withstand pressure. The cover 13 is lightly affixed to the receiver 14 by either clamps or the weight of the cover 13 alone.

The microwave chamber is penetrated by metal tubing at a point between valves 8 and 11, as well as between valves 10 and 12. A standard bulkhead fitting is used to ensure that the walls of the microwave chamber are electrically grounded to the metal tubing starting at the interior wall inward. The metal tubing must be tightly attached to the interior metal wall. If not, arcing or power transmission outside the walls of the microwave chamber can occur. If use of metal tubing is not desired, especially for the inlet side, plastic tubing can be used that will not absorb microwave energy but will withstand the temperature used. Of course, metal tubing serves to shield the liquid it contains from microwave heating. Plastic tubing, which would allow the contents of the tubing to absorb microwave energy, would have to be able to withstand the temperatures and pressures built up in the tubing due to the heating of the contents of the tubing. Therefore, metal tubing is preferred in general, even if the receiver 14 and cover 13 are both made from microwave transparent materials.

Other components that can be outfitted on or changes that can be made to the present invention include:

a) a spray nozzle for the water wash inlet to better disperse water over the instruments 17, thereby providing a better rinse;

b) spring activated check valves instead of ball valves to replace valves 11 and 12, to improve automation of the process;

c) attaching the receiver 14 to the cover 13 via a mechanism such as a hinge to provide a closeable receiver 14 and cover 13 that can be opened easily inside the microwave oven and the tray 16, therefore, easily removed;

d) preheating of the sterilization chemical in the microwave oven environment to a temperature that will not facilitate degradation of the sterilization chemical in order to reduce the time required to reach the specific temperature for sterilization;

e) lining a metal receiver 14 with glass or making the receiver 14 of dual wall construction in order to reduce heat transfer out of the receiver 14 during the sterilization heating process;

f) fabricating the receiver 14 in longer or wider dimensions in order to accommodate longer or more complex instruments 17;

g) using quick-connect fittings between valves 11, 12 and 18 and receiver 14 in order to accommodate the use of receivers 14 of varying dimensions;

h) making the receiver 14 with a non-flat bottom such that a low point can serve as a drain location;

i) making the tray 16 with a handle so that the tray 16 can be easily removed from the receiver 14;

j) using larger or multiple drain holes in order to reduce drain time;

k) using a source of pure dry air or dry nitrogen (non-toxic gas) to pass through the wet receiver 14 closed by the cover 13 in order to provide drying action; etc. The drier the receiver 14 and the inside surface of the cover 13, the less water that can reduce the concentration of the chemical used as a sterilant.

The present embodiment of the high temperature, non-conductive fluid, super heating fluid microwave sterilizer passes the sterilization chemical through the sterilization system once. An alternative embodiment, shown in FIG. 2, employs re-use of the sterilization chemical via distillation. In this embodiment, a container or select chemical reservoir 1 is filled with a sterilization chemical via a fill port 21. A second container or water reservoir 2 is filled with sterilized water. Valve 26 is used to control the flow of sterilization chemical and sterilized water to the receiver or fluid container (metal) 14. The receiver or fluid container (metal) 14 contains a microwave transparent window 24 and the fluid container 14 is partially covered with a cover or fluid condenser cap (metal) 13. The entire microwave process is controlled by a control and programming unit 25.

In this alternative embodiment, during times when the sterilization process is not being used, the microwave power is used to heat the contents of the select chemical reservoir 1, which are primarily a mixture of water and the sterilization chemical or mixture of sterilization chemicals. The microwave energy boils the mixture. The vapors from the mixture are distilled in the overhead condenser or distillation tower 23. In this process, the water is separated from the higher boiling chemical or chemicals.

When more than one chemical is used, either as an additive to the water or the sterilization chemical, the simple distillation device, depicted here for simplicity as a cold water condenser or distillation tower 23, is replaced by a fractional distillation column. A fractional distillation column separates two or more components.

Figure 2:
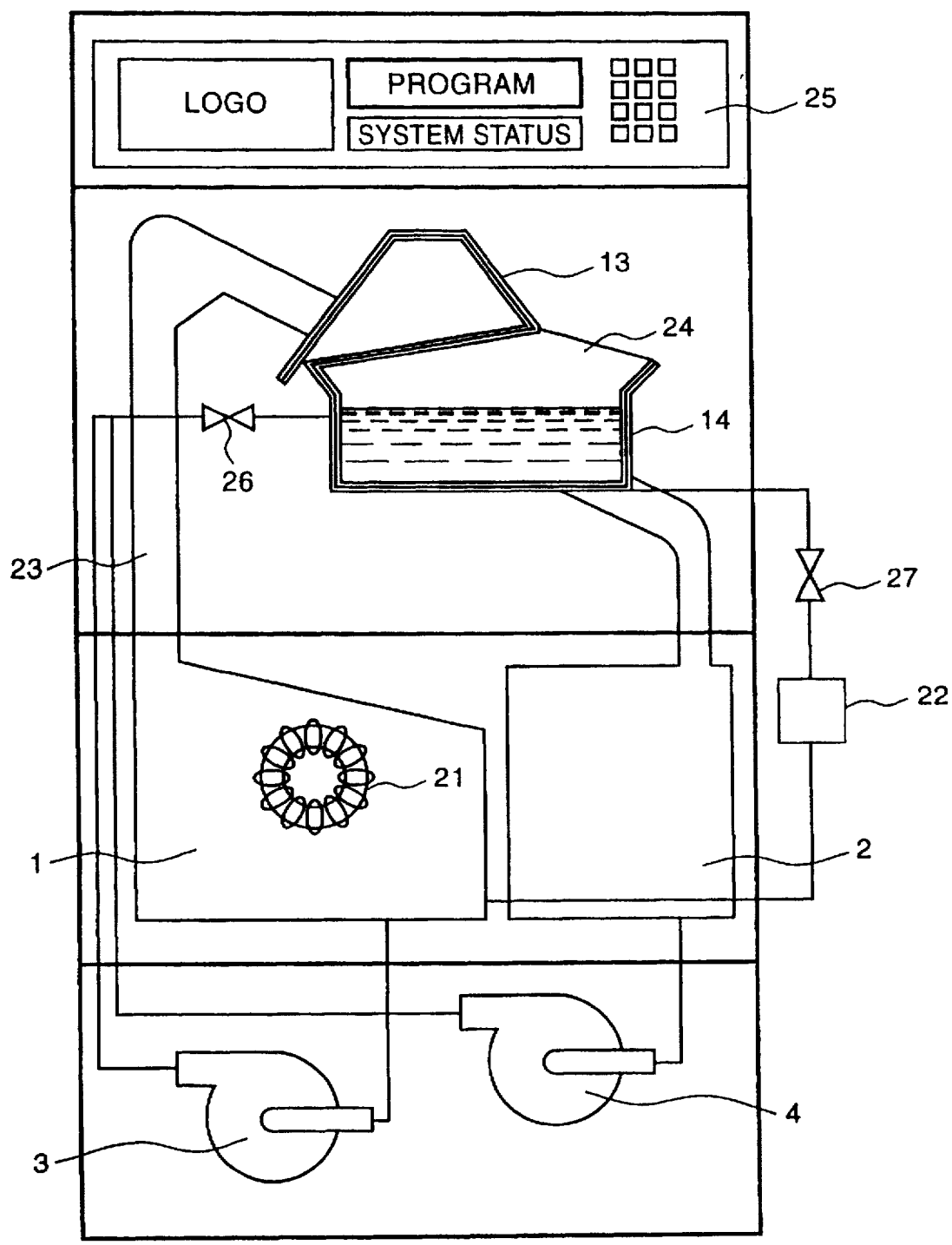
FIG. 2 shows a schematic representation of an alternative embodiment of the present invention that re-uses the sterilization chemical.

FIG. 2 includes a carbon/micropore filter 22 between the receiver or fluid container 14 and the select chemical reservoir 1 to remove particulates, such as tissue, cells, and microbes, as well as any chemical contaminants that would collect on a carbon filter. Valve 27 is used to control the flow of sterilization chemical between the receiver or fluid container 14 and the select chemical reservoir 1.

In yet another embodiment, the chemical regeneration task and the sterilization task can be accomplished simultaneously by use of a dual source system where the microwave power for each system is delivered separately. Such a system would be preferred for high use devices.

Many other design variations are possible, such that the door of the cavity used to contain the mechanism may open up or down. In addition, the door may be placed on the top of the unit, such that the unit may be situated on the floor rather than on a counter top or other support fixture. The receiver 14 has been depicted as being square and shallow, but it could just as well be round and/or tall, allowing sterilization of tools 17 in the upright position. The liquid inputs have been depicted as being on the side of the receiver 14, but they could also be placed in the cover 13.

EXAMPLES

The present invention can be further illustrated by the following non-limiting examples. In general, these examples show that the microwave heating of liquids to high temperatures can be used to sterilize medical instruments. In these examples, microbe sample strips commonly used for proof of sterility were employed. The microbes used were *Bacillus stearothermophilus* and *Bacillus subtilis*. The former microbe is resistant to steam sterilization conditions and the latter microbe is resistant to dry sterilization conditions.

Individually, the strips were submerged in sterilization chemical at room temperature. Test strips were then heated in a microwave oven to a preset temperature for one or two minutes in the chemical. Control strips were submerged in chemical for the same amount of total time, but not heated. The chemicals used were propylene glycol, tetraethylene glycol, polyethylene glycol, and glycerol.

Important attributes of the chemicals used are that they are removable from the medical tools after sterilization and/or that the chemical is non-hazardous. Table III provides the following toxicity information for some selected and related chemicals from The Condensed Chemical Dictionary, Tenth Edition, Van Nostrand Reinhold Company Inc., New York, 1981:

TABLE III

TOXICITY INFORMATION

| Compound | Information | Page No. |
|---|---|---|
| glycerol | low toxicity | 502 |
| glycerol monolaurate | nontoxic | 503 |
| glycerol monooleate | edible | 503 |
| glycerol monostearate | edible | 503 |
| polyethylene glycol | nontoxic | 831 |
| polygylcerol | low toxicity | 832 |
| 1,2-propylene glycol | nontoxic | 864 |
| propylene glycol monostearate | nontoxic | 865 |

Water was added in several examples to determine whether a small amount of water would be harmful to the procedure. The data from these examples is presented in detail below. Of note, the tetraethylene glycol performed less effectively in the sterilization process than the other three glycols. This result indicates that sterilization in the present process is not purely the result of a thermal phenomenon.

More specifically, 100 ml of the chemical used in the sterilization process, i.e., the sterilization chemical, was placed in a 400 ml beaker. The spore strip was then placed in the sterilization chemical and the beaker covered with a glass plate. The spore strips used were from *Bacillus stearothermophilus* and *Bacillus subtilis*. A corner of the *Bacillus subtilis* spore strip was cut in order to provide a means for visually differentiating between the two strips.

The covered beaker was placed into a CEM Corporation microwave oven. The temperature profile of a beaker containing 300 ml of glycol as a function of time exposed to microwaves in the oven is shown in Table IV.

TABLE IV

TEMPERATURE VERSUS TIME

| Elapsed Time (min:sec) | Pressure (psi) | Temperature (°C.) |
|---|---|---|
| 0:30 | –0002 | 62 |
| 0:45 | –0001 | 85 |
| 1:00 | –0002 | 108 |
| 1:15 | –0002 | 129 |
| 1:30 | –0002 | 148 |
| 1:45 | –0002 | 166 |
| 2:00 | –0002 | 184 |
| 2:15 | –0002 | 195 |
| 2:30 | –0002 | 193 |
| 2:45 | –0002 | 189 |

Figure 3:
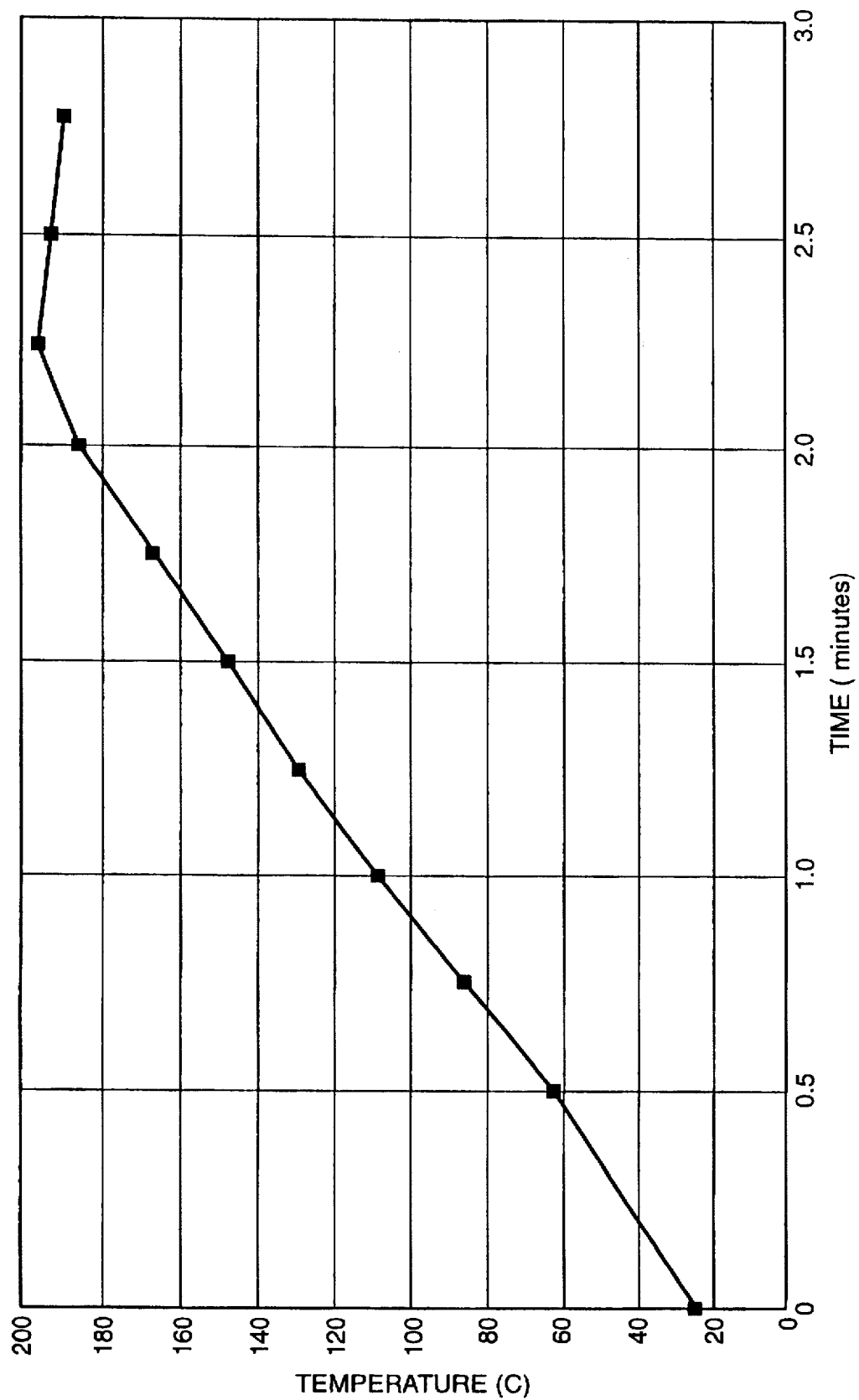
FIG. 3 shows the temperature rise of a beaker containing 300 ml of glycol as a function of time exposed to microwaves in a CEM Corporation microwave oven.

The same data as that presented in Table IV, i.e., the temperature rise of a beaker containing 300 ml of glycol as a function of time exposed to microwaves in the oven is presented graphically in FIG. 3.

The microwave oven was equipped with a built-in temperature probe that is used to reach and maintain desired temperatures. The temperature probe was placed in the sterilization chemical. A program with the appropriate hold temperature and the appropriate power setting was loaded into the microwave. The microwave door was closed and the microwave activated. The microwave was activated until the appropriate hold temperature was attained and then maintained for the appropriate maintenance time, i.e., one or two minutes.

After the appropriate time had elapsed, the microwave was deactivated and the beaker removed from the oven. The spore strip was removed from the sterilization chemical with sterile forceps and aseptically placed into a sterile thioglycolate vial. The thioglycolate vial was then incubated for 6-7 days at 55°-60° C. Some control thioglycolate vials were stored at room temperature to check for any mesophilic bacteria growth that may indicate contamination.

After the appropriate period of incubation, the thioglycolate vials were analyzed for bacterial growth. If the thioglycolate vial was clear, no viable bacteria were present. If the thioglycolate vial contained cloudy patches, viable bacteria were present. The growth of aerobic bacteria was suggested by cloudy patches found at the top of the thioglycolate.

Example 1

In Example 1, *Bacillus stearothermophilus* and *Bacillus subtilis* spore strips were placed in 100% propylene glycol and exposed to microwaves at various hold temperatures for either one or two minutes. There was no detectable bacterial growth for *Bacillus stearothermophilus* spore strips exposed to 100% propylene glycol at 140°, 150°, 160°, 170°, or 180° C. for one minute or at 150°, 160°, 170°, or 180° C. for two minutes. There was bacterial growth for *Bacillus stearothermophilus* spore strips exposed to 100% propylene glycol at 140° C. for two minutes.

There was no detectable bacterial growth for *Bacillus subtilis* spore strips exposed to 100% propylene glycol at 140°, 150°, 160°, 170°, or 180° C. for either one or two minutes. These results are presented in Table V.

Example 2

In Example 2, *Bacillus stearothermophilus* and *Bacillus subtilis* spore strips were placed in 98% propylene glycol (i.e., 2% water, v/v) and exposed to microwaves at various hold temperatures for either one or two minutes. There was no detectable bacterial growth for either *Bacillus stearothermophilus* or *Bacillus subtilis* spore strips exposed to 98% propylene glycol at 150°, 160°, 170° or 180° C. for either one or two minutes.

There was bacterial growth for both *Bacillus stearothermophilus* and *Bacillus subtilis* spore strips exposed to 98% propylene glycol at 140° C. for either one or two minutes. These results are presented in Table VI.

Example 3

In Example 3, *Bacillus stearothermophilus* and *Bacillus subtilis* spore strips were placed in 95% propylene glycol (i.e., 5% water, v/v) and exposed to microwaves at various hold temperatures for either one or two minutes. There was no detectable bacterial growth for *Bacillus stearothermophilus* spore strips exposed to 95% propylene glycol at 160°, 170°, or 180° C. for either one or two minutes. There was bacterial growth for *Bacillus stearothermophilus* spore strips exposed to 95% propylene glycol at 140° or 150° C. for either one or two minutes.

There was no detectable bacterial growth for *Bacillus subtilis* spore strips exposed to 95% propylene glycol at 150°, 160°, 170°, or 180° C. for one minute or at 160°, 170°, or 180° C. for two minutes. There was bacterial growth for *Bacillus subtilis* spore strips exposed to 95% propylene glycol at 140° C. for one minute or at 140°or 150° C. for two minutes. These results are presented in Table VII.

Example 4

In Example 4, *Bacillus stearothermophilus* and *Bacillus subtilis* spore strips were placed in 100% tetraethylene glycol and exposed to microwaves at various hold temperatures for one minute. There was no detectable bacterial growth only for *Bacillus stearothermophilus* spore strips exposed to 100% tetraethylene glycol at 190° C. for one minute. There was detectable bacterial growth for *Bacillus stearothermophilus* spore strips exposed to 100% tetraethylene glycol at 145°, 160°, or 175° C. for one minute or for *Bacillus subtilis* spore strips exposed to 100% tetraethylene glycol at 145°, 160°, 175°, or 190° C. for one minute. These results are presented in Table VIII.

Example 5

In Example 5, *Bacillus stearothermophilus* and *Bacillus subtilis* spore strips were placed in 100% polyethylene glycol and exposed to microwaves at various hold temperatures for either one or two minutes. There was no detectable bacterial growth for *Bacillus stearothermophilus* spore strips exposed to 100% polyethylene glycol at 145°, 160°, 175°, or 190° C. for one minute or at 145°, 175°, or 190° C. for two minutes. There was detectable bacterial growth for *Bacillus stearothermophilus* spore strips exposed to 100% polyethylene glycol at 160° C. for two minutes.

There was no detectable bacterial growth for *Bacillus subtilis* spore strips exposed to 100% polyethylene glycol at 160°, 175°, or 190° C. for one minute or at 145°, 160°, 175°, or 190° C. for two minutes. There was bacterial growth detected for *Bacillus subtilis* spore strips exposed to 100% polyethylene glycol at 145° C. for one minute. These results are presented in Table IX.

Example 6

In Example 6, *Bacillus stearothermophilus* and *Bacillus subtilis* spore strips were placed in 95% polyethylene glycol (i.e., 5% water, v/v) and exposed to microwaves at various hold temperatures for either one or two minutes. There was no detectable bacterial growth for *Bacillus stearothermophilus* spore strips exposed to 95% polyethylene glycol at 160°, 175°, or 190° C. for either one or two minutes. There was bacterial growth for *Bacillus stearothermophilus* spore strips exposed to 95% polyethylene glycol at 145° C. for either one or two minutes.

There was no detectable bacterial growth for *Bacillus subtilis* spore strips exposed to 95% polyethylene glycol at 145°, 160°, 175°, or 190° C. for one minute or at 175° or 190° C. for two minutes. There was bacterial growth for *Bacillus subtilis* spore strips exposed to 95% polyethylene glycol at 145° or 160° C. for two minutes. These results are presented in Table X.

Example 7

In Example 7, *Bacillus stearothermophilus* and *Bacillus subtilis* spore strips were placed in 100% glycerol and exposed to microwaves at various hold temperatures for either one or two minutes. There was no detectable bacterial growth for *Bacillus stearothermophilus* spore strips exposed to 100% glycerol at 145°, 160°, 175°, or 190° C. for one minute or at 160°, 175°, or 190° C. for two minutes. There was bacterial growth for *Bacillus stearothermophilus* spore strips exposed to 100% glycerol at 145° C. for two minutes.

There was no detectable bacterial growth for *Bacillus subtilis* spore strips exposed to 100% glycerol at 160°, 175°, or 190° C. for either one or two minutes. There was bacterial growth detected for *Bacillus subtilis* spore strips exposed to 100% glycerol at 145° C. for either one or two minutes. These results are presented in Table XI.

Example 8

In Example 8, *Bacillus stearothermophilus* and *Bacillus subtilis* spore strips were placed in 95% glycerol (i.e., 5% water, v/v) and exposed to microwaves at various hold temperatures for either one or two minutes. There was no detectable bacterial growth for *Bacillus stearothermophilus* spore strips exposed to 95% glycerol at 160°, 175°, or 190° C. for either one or two minutes. There was bacterial growth for *Bacillus stearothermophilus* spore strips exposed to 95% glycerol at 145° C. for either one or two minutes.

There was no detectable bacterial growth for *Bacillus subtilis* spore strips exposed to 95% glycerol at 160°, 175°, or 190° C. for either one or two minutes. There was bacterial growth for *Bacillus subtilis* spore strips exposed to 95% glycerol at 145° C. for either one or two minutes. These results are presented in Table XII.

The results presented in Examples 1–8 show that the present invention can be used for sterilization and that small amounts of water, i.e., less than 10% by volume, in the sterilization chemical are not harmful to the atmospheric pressure, microwave sterilization process of the present invention.

In summary, the high temperature, non-conductive fluid, super heating fluid microwave sterilizer of the present invention offers the following advantages over the conventional autoclave sterilizer:

a) up to six times faster sterilization cycle;

b) safer operation at atmospheric pressure (no dangerous steam);

c) safer operation since less mass is heated (no thermal contact burns with oven);

d) use of non-conductive liquids (retains instrument integrity longer due to suppression of arcing);

e) simpler to operate than conventional equipment (press a few clearly labeled buttons);

f) sterile temperatures are positively exceeded (optional built in temperature strip and/or fiber optic thermometer); and g) enhanced tool sharpness life (due to suppressed water catalyzed oxidation, the oxygen absorbed by water, especially at high pressures, and cavitation caused by prolonged boiling).

While the invention has been described in connection with what is presently considered to be the most practical and preferred embodiments, it is to be understood that the invention is not limited to the disclosed embodiments, but on the contrary is intended to cover various modifications and equivalent arrangements included within the spirit and scope of the appended claims.

Thus, it is to be understood that variations in the present invention can be made without departing from the novel aspects of this invention as defined in the claims. All patents and scientific articles cited herein are hereby incorporated by reference in their entirety and relied upon.

TABLE V

BACTERIAL GROWTH TESTS IN MICROWAVED GLYCOLS

| Chemical: Propylene Glycol | Concentration: 100% | | | Microwave: CEM @ 100% | | |
|---|---|---|---|---|---|---|
| Time exposed to set temperatue | 1 minute | | | 2 minutes | | |
| | Spore | | | | | |
| Set Temp C. | High Temp | D | S | High Temp | D | S |
| 140 | – | – | – | + | – | |
| 150 | – | – | – | – | – | |
| 160 | – | – | – | – | – | |
| 170 | – | – | – | – | – | |
| 180 | – | – | – | – | – | |

D: Dry sterilization indicator, *Bacillus stearothermophilus*
S: Steam sterilization indicator, *Bacillus subtilis*
Negative Bacteria Growth  –
Positive Bacteria Growth  +

TABLE VI

BACTERIAL GROWTH TESTS IN MICROWAVED GLYCOLS

| Chemical: Propylene Glycol | Concentration: 98% | | | Microwave: CEM @ 100% | | |
|---|---|---|---|---|---|---|
| Time exposed to set temperatue | 1 minute | | | 2 minutes | | |
| | Spore | | | | | |
| Set Temp C. | High Temp | D | S | High Temp | D | S |
| 140 | | + | + | | + | + |
| 150 | | – | – | | – | – |
| 160 | | – | – | | – | – |
| 170 | | – | – | | – | – |
| 180 | | – | – | | – | – |

D: Dry sterilization indicator, *Bacillus stearothermophilus*
S: Steam sterilization indicator, *Bacillus subtilis*
Negative Bacteria Growth  –
Positive Bacteria Growth  +

TABLE VII

BACTERIAL GROWTH TESTS IN MICROWAVED GLYCOLS

| Chemical: Propylene Glycol | Concentration: 95% | | | Microwave: CEM @ 100% | | |
|---|---|---|---|---|---|---|
| Time exposed to set temperatue | 1 minute | | | 2 minutes | | |
| | Spore | | | | | |
| Set Temp C. | High Temp | D | S | High Temp | D | S |
| 140 | | + | + | | + | + |
| 150 | | + | – | | + | + |
| 160 | | – | – | | – | – |
| 170 | | – | – | | – | – |
| 180 | | – | – | | – | – |

D: Dry sterilization indicator, *Bacillus stearothermophilus*
S: Steam sterilization indicator, *Bacillus subtilis*
Negative Bacteria Growth  –
Positive Bacteria Growth  +

TABLE VIII

BACTERIAL GROWTH TESTS IN MICROWAVED GLYCOLS

Chemical: Tetraethylene Glycol  
Concentration: 100%  
Microwave: CEM @ 100%  
Time exposed to set temperature: 1 minute / 2 minutes

| Set Temp C. | Spore High Temp | D | S | High Temp | D | S |
|---|---|---|---|---|---|---|
| 145 |  | + | + |  | NM | NM |
| 160 |  | + | + |  | NM | NM |
| 175 |  | + | + |  | NM | NM |
| 190 |  | − | + |  | NM | NM |

D: Dry sterilization indicator, *Bacillus stearothermophilus*  
S: Steam sterilization indicator, *Bacillus subtilis*  
Negative Bacteria Growth  −  
Positive Bacteria Growth  +  
Not Measured  NM

TABLE IX

BACTERIAL GROWTH TESTS IN MICROWAVED GLYCOLS

Chemical: Polyethylene Glycol (Mn = 400)  
Concentration: 100%  
Microwave: CEM @ 100%  
Time exposed to set temperature: 1 minute / 2 minutes

| Set Temp C. | Spore High Temp | D | S | High Temp | D | S |
|---|---|---|---|---|---|---|
| 145 |  | − | + |  | − | − |
| 160 |  | − | − |  | + | − |
| 175 |  | − | − |  | − | − |
| 190 |  | − | − |  | − | − |

D: Dry sterilization indicator, *Bacillus stearothermophilus*  
S: Steam sterilization indicator, *Bacillus subtilis*  
Negative Bacteria Growth  −  
Positive Bacteria Growth  +

TABLE X

BACTERIAL GROWTH TESTS IN MICROWAVED GLYCOLS

Chemical: Polyethylene Glycol (Mn = 400)  
Concentration: 95%  
Microwave: CEM @ 100%  
Time exposed to set temperature: 1 minute / 2 minutes

| Set Temp C. | Spore High Temp | D | S | High Temp | D | S |
|---|---|---|---|---|---|---|
| 145 |  | + | − |  | + | + |
| 160 |  | − | − |  | − | + |
| 175 |  | − | − |  | − | − |
| 190 |  | − | − |  | − | − |

D: Dry sterilization indicator, *Bacillus stearothermophilus*  
S: Steam sterilization indicator, *Bacillus subtilis*  
Negative Bacteria Growth  −  
Positive Bacteria Growth  +

TABLE XI

BACTERIAL GROWTH TESTS IN MICROWAVED GLYCOLS

Chemical: Glycerol  
Concentration: 100%  
Microwave: CEM @ 100%  
Time exposed to set temperature: 1 minute / 2 minutes

| Set Temp C. | Spore High Temp | D | S | High Temp | D | S |
|---|---|---|---|---|---|---|
| 145 |  | − | + |  | + | + |
| 160 |  | − | − |  | − | − |
| 175 |  | − | − |  | − | − |
| 190 |  | − | − |  | − | − |

D: Dry sterilization indicator, *Bacillus stearothermophilus*  
S: Steam sterilization indicator, *Bacillus subtilis*  
Negative Bacteria Growth  −  
Positive Bacteria Growth  +

TABLE XII

BACTERIAL GROWTH TESTS IN MICROWAVED GLYCOLS

Chemical: Glycerol  
Concentration: 95%  
Microwave: CEM @ 100%  
Time exposed to set temperature: 1 minute / 2 minutes

| Set Temp C. | Spore High Temp | D | S | High Temp | D | S |
|---|---|---|---|---|---|---|
| 145 |  | + | + |  | + | + |
| 160 |  | − | − |  | − | − |
| 175 |  | − | − |  | − | − |
| 190 |  | − | − |  | − | − |

D: Dry sterilization indicator, *Bacillus stearothermophilus*  
S: Steam sterilization indicator, *Bacillus subtilis*  
Negative Bacteria Growth  −  
Positive Bacteria Growth  +

What is claimed is:

1. An apparatus for sterilizing instruments at atmospheric pressure in a microwave oven in less than ten minutes, comprising:

a) a tray for holding instruments to be sterilized, b) a receiver for holding the tray, the receiver being connected to a first container, a second container and a third container, wherein the first container holds a sterilization chemical for transfer to the receiver, the second container holds water for transfer to the receiver, and the third container holds sterilization chemical and water for transfer from the receiver, wherein the sterilization chemical has a boiling point greater than 100° C., c) a cover for placement over the tray, d) a first pump to transfer sterilization chemical to the receiver, e) a second pump to transfer water to the receiver, and f) a microwave oven, wherein the apparatus is configured to operate for sterilizing instruments at atmospheric pressure and wherein the sterilization process is completed in less than ten minutes.

2. The apparatus of claim 1, wherein a first valve is used to control the transfer of sterilization chemical to the receiver, a second valve is used to control the transfer of water to the receiver, and a third valve is used to control the transfer of sterilization chemical and water from the receiver.

3. The apparatus of claim 1, wherein the tray, the receiver or the cover is made from a microwave transparent material.

4. The apparatus of claim 3, wherein the microwave transparent material is selected from the group consisting of glass, plastic, and ceramic.

5. The apparatus of claim 3, wherein the microwave transparent material is selected from the group consisting of polyetherimides, polyimides, Kalrez (™), polytetrafluoroethylene, quartz, Pyrex glass, and dense aluminum oxide.

6. The apparatus of claim 1, wherein the tray, the receiver or the cover is made from a metal.

7. The apparatus of claim 6, wherein the metal is stainless steel.

8. The apparatus of claim 1, wherein the tray and the receiver are made from stainless steel and the cover is made from borosilicate glass.

9. The apparatus of claim 8, wherein a metal strip is connected to the stainless steel tray and to the instruments.

10. An atmospheric pressure, microwave sterilization process, wherein the sterilization process in completed in less than ten minutes, comprising the steps of:

a) placing instruments in a microwave oven;

b) immersing the instruments in a sterilization chemical, wherein the sterilization chemical has a boiling point greater than 100° C.;

c) subjecting the instruments in the sterilization chemical to microwave heating, wherein pressure is not contained during the sterilization process and wherein the sterilization process is completed in less than ten minutes;

d) terminating the microwave heating;

e) draining the sterilization chemical from the instruments;

f) rinsing the instruments with sterilized water;

g) draining the sterilized water from the instruments; and h) recovering sterilized instruments from the microwave oven.

11. The method of claim 10, wherein the sterilization chemical has a boiling point of at least 121° C.

12. The method of claim 10, wherein the sterilization chemical has a boiling point of at least 140° C.

13. The method of claim 10, wherein the sterilization chemical is at least slightly soluble in water.

14. The method of claim 10, wherein the sterilization chemical is rinsable in water.

15. The method of claim 10, wherein the sterilization chemical is selected from the group consisting of polyethylene glycol, propylene glycol, glycerin, di(propylene glycol), 2,2-dimethyl-1-3,butanediol, triethylene glycol, tetraethylene glycol, dimethyl sulfoxide, triethanolamine, triethylcitrate, tetrahydrofurfuryl acetate, thiodiglycol, propyleneglycol phenyl ether, 1-heptanol, methane sulfonic acid, diethylene triamine, N,N-dimethylformamide, glutaraldehyde, propiolactone, and diiodomethane.

16. The method of claim 10, wherein the sterilization chemical is selected from the group consisting of glycerol monolaurate, glycerol monooleate, glycerol monostearate, polygylcerol, and propylene glycol monostearate.

17. The method of claim 10, wherein the sterilization chemical is selected from the group consisting of oils, resins, waxes, flavorants, gums, or essential oils.

18. The method of claim 10, wherein the sterilization chemical contains an additive to facilitate rinsing away the sterilization chemical from the instruments.

19. The method of claim 18, wherein the sterilization chemical contains less than 10% additive by volume.

20. The method of claim 18, wherein said additive is ethanol or diethylether.

21. The method of claim 10, wherein the microwave sterilization process is completed in less than six minutes.

22. The method of claim 10, wherein the sterilization chemical contains less than 10% water by volume.

* * * * *